US00PP19897P2

(12) United States Plant Patent

Bennato Chez

(10) Patent No.: US PP19,897 P2

(45) Date of Patent: Apr. 7, 2009

(54) *HAKONECHLOA* PLANT NAMED 'NAOMI'

(50) Latin Name: *Hakonechloa macra*
Varietal Denomination: Naomi

(76) Inventor: Olivier Bennato Chez, 203 Avenue De Pépinières Fleurs 515, Min Rungis Cedex (FR), 94648

( * ) Notice: Subject to any disclaimer, the term of this patent is extended or adjusted under 35 U.S.C. 154(b) by 0 days.

(21) Appl. No.: 12/079,983

(22) Filed: Mar. 31, 2008

(51) Int. Cl.
*A01H 5/00* (2006.01)

(52) U.S. Cl. ..... Plt./384

(58) Field of Classification Search ..... Plt./384
See application file for complete search history.

*Primary Examiner*—Annette H Para
(74) *Attorney, Agent, or Firm*—Penny J. Aguirre

(57) ABSTRACT

A new and unique cultivar of *Hakonechloa* named 'Naomi' that is characterized by its variegated foliage that is creamy white to yellow green with green bands in the spring and summer and turning deep red to deep purple in fall. As the mature foliage changes to a red and purple with cool temperatures, a combination of summer and fall foliage creates a unique combination of foliage color. 'Naomi' is further characterized by its dwarf plant habit, its hardiness in U.S.D.A. Zones 5 to 9, and its relatively vigorous growth habit.

2 Drawing Sheets

RELATED APPLICATIONS

This application is co-pending with U.S. Plant Patent application No. 12/080,053 filed for a cultivar selected by the same inventor entitled Hakonechloa Plant Named 'Nicolas'.

Botanical classification: *Hakonechloa macra.*

Varietal designation: 'Naomi'.

BACKGROUND OF THE INVENTION

The present invention relates to a new and distinct cultivar of *Hakonechloa macra* and will be referred to hereafter by its cultivar name, 'Naomi'. 'Naomi' represents a new cultivar of Hakone grass, an ornamental grass grown for landscape use.

The inventor discovered the new cultivar, 'Naomi', in a cultivated trial garden in Min Rungis Cedex, France as a naturally occurring whole plant mutation in fall of 2003. The inventor had been growing and selecting unnamed seedlings of *Hakonechloa macra* in his trail garden for many years and therefore, the parent plants of 'Naomi' are unknown.

Asexual reproduction of the new cultivar was first accomplished by stem division in Min Rungis Cedex, France in spring 2004 by the inventor. The characteristics of this cultivar have been determined to be stable and are reproduced true to type in successive generations.

SUMMARY OF THE INVENTION

The following traits have been repeatedly observed and represent the characteristics of the new cultivar as grown outdoors in a trial garden for five years in Min Rungis Cedex, France. These attributes in combination distinguish 'Naomi' as a unique cultivar of *Hakonechloa.*

1. 'Naomi' exhibits variegated foliage that is creamy white to yellow green with green bands in the spring and summer and turning deep red to deep purple in fall. As the mature foliage changes to a red purple color with cool temperatures, a combination of summer and fall foliage creates a unique combination of foliage color.

2. 'Naomi' exhibits a dwarf plant habit reaching about 35 cm in height in bloom with the foliage reaching 25 cm in height.
3. 'Naomi' is suitable for use as an edging and groundcover plant.
4. 'Naomi' is hardy in U.S.D.A. Zones 5 to 9.
5. 'Naomi' blooms in summer with airy panicles above the foliage.

'Naomi' can be most closely compared to *Hakonechloa macra* 'Aureola' (unpatented) and 'Nicolas', another cultivar selected by the inventor. 'Aureola' has similar leaf variegation, however the fall color of 'Aureola' is a less intense, is more red than purple in color and has a less vigorous growth habit. 'Nicolas' is similar to 'Naomi' in height and also attains an intense red fall color, however the summer foliage of 'Nicolas' is green and non-variegated and the fall color is less purple in color.

BRIEF DESCRIPTION OF THE DRAWING

The accompanying colored photographs illustrate the overall appearance and distinct characteristics of the new *Hakonechloa.*

The photograph on the first sheet was taken in October of a 3 year old plant of 'Naomi' as grown in a trial garden in The Netherlands and illustrates the purple coloration of 'Naomi'.

The photographs on the second sheet were taken in late summer of 3 year-old plants of 'Naomi' as grown in a 26 cm container in The Netherlands.

The photograph on the top of the second sheet is a close-up view of the foliage with a combination of yellow summer foliage and fall red foliage.

The photograph on the bottom of the second sheet provides a close-up view of the flower panicles.

The colors in the photographs are as close as possible with the digital photography techniques available, the color values cited in the detailed botanical description accurately describe the colors of the new *Hakonechloa*.

BOTANICAL DESCRIPTION OF THE PLANT

The following is a detailed description of 3 year-old plants of 'Naomi' as grown outdoors in 26 cm containers in The Netherlands. The plants were grown in average day temperatures of 13° to 27° C. and average night temperatures of 4° to 14° C. under ambient light. The phenotype of the new cultivar may vary with variations in environmental, climatic, and cultural conditions, as it has not been tested under all possible environmental conditions. The color determination is in accordance with the 2001 R.H.S. Colour Chart of the Royal Horticultural Society, London, England, except where general color terms of ordinary dictionary significance are used.

General description:

*Blooming habit.*—Blooms in mid summer.

*Plant habit.*—Herbaceous, clump-forming, slowly spreading ornamental grass forming a mound of bamboo-like cascading foliage, suitable for use as a groundcover or edging plant.

*Height and spread.*—Exhibits a dwarf plant habit reaching about 35 cm in height in bloom with the foliage reaching 25 cm in height and a spread of about 66 cm.

*Hardiness.*—U.S.D.A. Zones 5 to 9.

*Culture.*—Performs best in moist, well drained, organic rich soils in partial or part shade.

*Diseases and pests.*—No susceptibility or resistance to diseases or pests has been observed.

*Root description.*—Fibrous.

Growth and propagation:

*Propagation.*—Tissue culture and stem division.

*Vigor.*—More vigorous than is typical of *Hakonechloa macra* selections with colored and variegated foliage.

Culm (stem) description:

*General.*—Round, sheathed.

*Culm color.*—146B to 146C and tinged with 183C near nodes.

*Culm size.*—Average of 15.3 cm in length and 1 m in length.

*Stem surface.*—Glabrous, slightly glossy.

*Stem number.*—About 250 (3 year-old plant).

*Internode length.*—Average of 3.2 cm.

*Branching.*—Basal branches only, no lateral branches.

Foliage description:

*Leaf shape.*—Linear.

*Leaf division.*—Simple.

*Leaf base.*—Cuneate and decurrent at stem.

*Leaf apex.*—Acuminate.

*Leaf aspect.*—Held from horizontal to cascading downward.

*Leaf venation.*—Parallel, color on upper surface 143B to 143C on main veins with secondary veins matching leaf color, color on lower surface matches leaf color.

*Leaf margin.*—Entire, with sharp short bristles that are not visually noticeable.

*Leaf attachment.*—Sheathed.

*Leaf size.*—Average of 1 cm in width and 14.7 cm in length.

*Leaf number.*—Average of 5 per culm.

*Leaf arrangement.*—Alternate

*Ligule.*—A band of tufted hairs, 1 mm in length and N155A in color.

*Leaf surface.*—Glabrous and slightly glossy on upper and lower surface with bristles on margins.

*Leaf color.*—Young leaves, upper surface; N144B to N144C with stripes 143A to 143B, young leaves, lower surface; N144D with stripes 143B to 144A, mature leaves, upper surface; 153D to 155C (depending on light) with stripes 143B to 143C and heavily tinged with colors ranging from red tones of 176A to 176C to purple tones from N77A to N77C, mature leaves, lower surface; 153D to 155C (depending on light) with stripes 143C to 143D and tinged with colors ranging from red tones of 176A to 176C to purple tones from N77A to N77C, stripes vary in width from 0.5 to 4 mm and cover an average of 25% of the leaf area. The color ranges stated are dependent on temperature and light levels.

Inflorescence description:

*General description.*—Terminal airy panicle of single spikelets.

*Lastingness of inflorescence.*—Each panicle blooms for about 3 weeks, persistent.

*Fragrance.*—None.

*Panicle size.*—Average of 11.6 cm in length and up to 8.5 cm in width.

*Panicle number.*—One per culm.

*Rachis size.*—Up to about 10.5 cm in length, continuous with culm, 0.8 mm in diameter, with rachilla emerging at about a 50° angle to main branch about 7 cm in length and less than 0.8 mm in diameter, N144A in color.

*Spikelet bud.*—About 9 mm in length and 1 mm in width, narrow lanceolate in shape, 145C to 145D in color.

*Spikelet description.*—Single floret enclosed by one glume and one lemma, glume; lanceolate in shape with a glabrous surface, entire margin, acute apex, 4 mm in length, 0.5 mm in width and 144C to 144D in color with the tip 181 B to 181C, lemma; lanceolate in shape with a glabrous surface, entire margin, acute apex, 7 mm in length, 1 mm in width and 144C to 144D in color with the tip 181 B to 181C.

*Spikelet number.*—About 225 per panicle.

*Spikelet size.*—About 9 mm in length and 3 mm in width.

Reproductive organs:

*Stamens.*—2, anthers are dorsifixed, x-shaped, about 2 mm in length and 187A to 187B in color, pollen is low in quantity and 162A to 162D in color.

*Pistils.*—2, about 1.5 mm in length, stigma is fimbriate in shape, about 0.5 mm in length, and N77C in color, style; transparent in color, about 0.5 mm in length, ovary is 145A in color.

*Seed.*—No seed development has been observed.

It is claimed:

1. A new and distinct cultivar of *Hakonechloa* plant named 'Naomi' as herein illustrated and described.

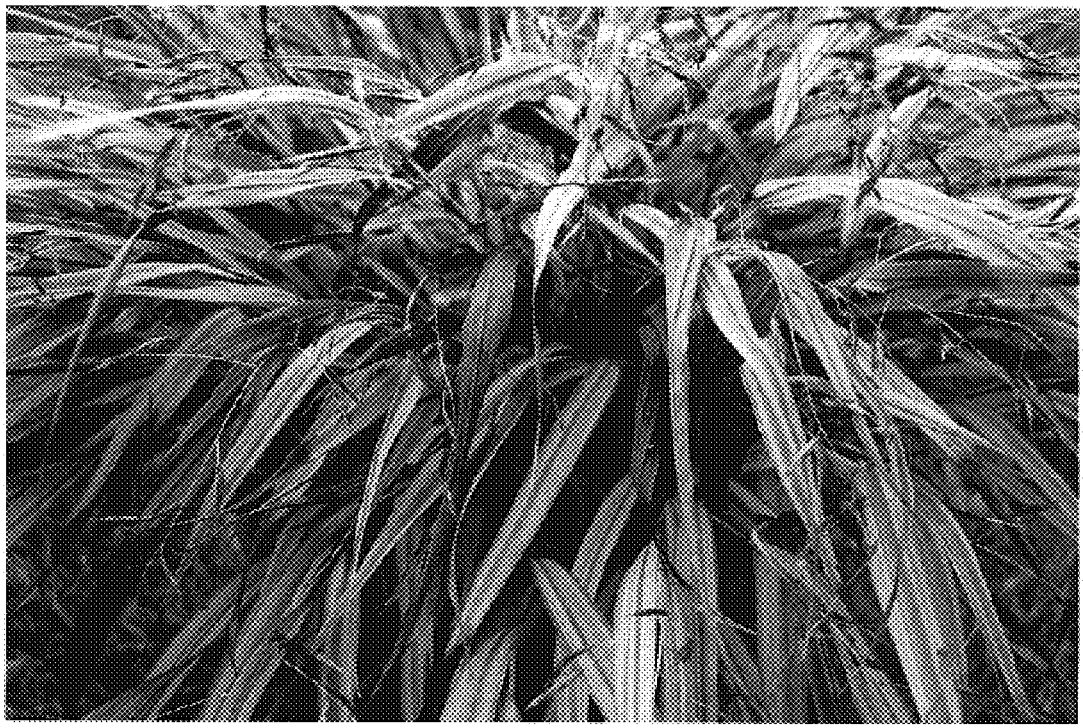

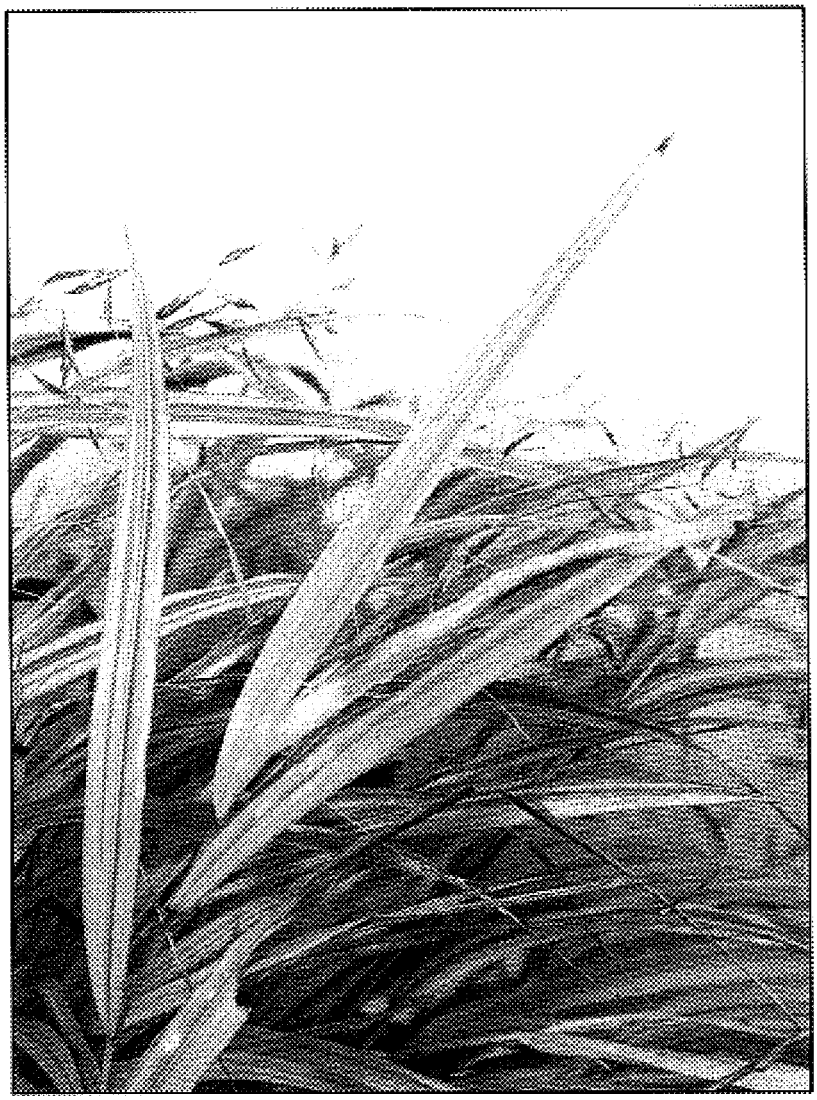
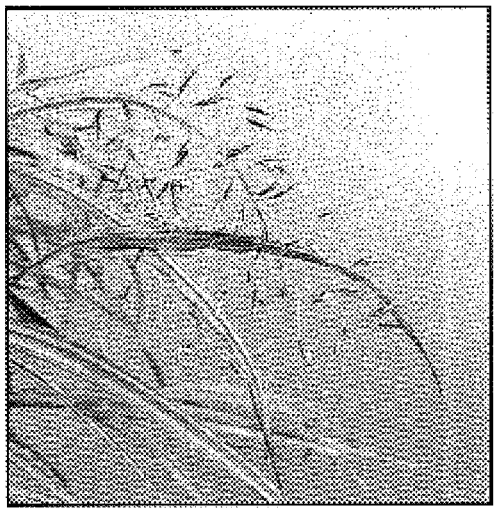

* * * * *